United States Patent
Teuma et al.

(10) Patent No.: US 11,607,339 B2
(45) Date of Patent: Mar. 21, 2023

(54) LASER METHODS AND SYSTEMS FOR ADDRESSING, MITIGATING AND REVERSING PRESBYOPIA

(71) Applicant: Lensar, Inc., Orlando, FL (US)

(72) Inventors: E. Valaski Teuma, Orlando, FL (US); Gary P. Gray, Orlando, FL (US)

(73) Assignee: Lensar, Inc., Orlando, FL (US)

( * ) Notice: Subject to any disclaimer, the term of this patent is extended or adjusted under 35 U.S.C. 154(b) by 134 days.

(21) Appl. No.: 16/290,904

(22) Filed: Mar. 2, 2019

(65) Prior Publication Data

US 2019/0298573 A1    Oct. 3, 2019

Related U.S. Application Data

(60) Provisional application No. 62/637,452, filed on Mar. 2, 2018.

(51) Int. Cl.
| | | |
|---|---|---|
| A61F 9/008 | (2006.01) |
| A61B 18/00 | (2006.01) |
| A61B 18/20 | (2006.01) |
| A61B 17/00 | (2006.01) |

(52) U.S. Cl.
CPC .. *A61F 9/00838* (2013.01); *A61B 2017/0019* (2013.01); *A61B 2018/00702* (2013.01); *A61B 2018/20355* (2017.05); *A61F 2009/0087* (2013.01); *A61F 2009/00895* (2013.01); *A61F 2009/00897* (2013.01)

(58) Field of Classification Search
None
See application file for complete search history.

(56) References Cited

U.S. PATENT DOCUMENTS

| | | | |
|---|---|---|---|
| 4,538,608 | A | 9/1985 | L'Esperance |
| 4,764,930 | A | 8/1988 | Bille |
| 4,901,718 | A | 2/1990 | Bille |
| 4,907,586 | A | 3/1990 | Bille |
| 5,098,426 | A | 3/1992 | Sklar |
| 5,246,435 | A | 9/1993 | Bille |
| 5,355,181 | A | 10/1994 | Ashizaki |
| 5,439,462 | A | 8/1995 | Bille |
| 5,480,396 | A | 1/1996 | Simon |
| 6,004,314 | A | 12/1999 | Wei |
| 6,099,522 | A | 8/2000 | Knopp |
| 6,197,018 | B1 | 3/2001 | O'Donnell |
| 6,312,422 | B1 | 6/2001 | Dubnack |
| 6,322,556 | B1 | 11/2001 | Gwon |
| 6,325,792 | B1 | 12/2001 | Swinger |
| 7,655,002 | B2 | 2/2010 | Myers |
| 8,262,646 | B2 | 9/2012 | Frey |

(Continued)

OTHER PUBLICATIONS

Cite No.
Sig Nat.

*Primary Examiner* — Carl H Layno
*Assistant Examiner* — Manolis Pahakis
(74) *Attorney, Agent, or Firm* — Glen P. Belvis; Belvis Law, LLC.

(57) ABSTRACT

Systems and methods for performing laser operations to improve the accommodative amplitude of an eye. Systems, methods and laser delivery patterns and operations for structural pillars in the lens of the eye to permit deformation of laser effected areas of the lens that are adjacent to the pillars.

13 Claims, 11 Drawing Sheets

(56) References Cited

U.S. PATENT DOCUMENTS

| | | | |
|---|---|---|---|
| 8,382,745 B2* | 2/2013 | Naranjo-Tackman | A61F 9/008 606/4 |
| 8,394,084 B2 | 3/2013 | Palankar et al. | |
| 8,403,921 B2 | 3/2013 | Palankar et al. | |
| 8,425,497 B2 | 4/2013 | Blumenkranz et al. | |
| 8,465,478 B2* | 6/2013 | Frey | A61F 9/008 606/4 |
| 8,480,659 B2 | 7/2013 | Frey | |
| 8,500,723 B2 | 8/2013 | Frey | |
| 8,617,146 B2 | 12/2013 | Frey | |
| 8,758,332 B2* | 6/2014 | Frey | A61F 9/00825 606/4 |
| 8,801,186 B2 | 8/2014 | Frey | |
| 9,180,051 B2 | 11/2015 | Frey | |
| 9,375,349 B2* | 6/2016 | Frey | A61F 9/008 |
| 9,545,338 B2* | 1/2017 | Frey | A61F 9/008 |
| 9,889,043 B2* | 2/2018 | Frey | A61F 9/00827 |
| 9,968,485 B2 | 5/2018 | Potter | |
| 10,213,340 B2 | 2/2019 | Gray | |
| 10,709,610 B2 | 7/2020 | Morley | |
| 11,090,190 B2 | 8/2021 | Morley | |
| 2002/0103478 A1 | 8/2002 | Gwon | |
| 2004/0199149 A1* | 10/2004 | Myers | A61F 9/008 623/6.22 |
| 2006/0195076 A1* | 8/2006 | Blumenkranz | A61F 9/00812 606/4 |
| 2007/0173794 A1 | 7/2007 | Frey | |
| 2007/0185475 A1 | 8/2007 | Frey | |
| 2008/0287928 A1 | 11/2008 | Arnoldussen | |
| 2010/0004641 A1 | 1/2010 | Frey | |
| 2010/0292678 A1* | 11/2010 | Frey | A61F 9/008 606/5 |
| 2011/0077624 A1* | 3/2011 | Brady | A61F 9/00736 606/4 |
| 2011/0190739 A1 | 8/2011 | Frey | |
| 2012/0016350 A1* | 1/2012 | Myers | A61F 9/008 606/4 |
| 2012/0172852 A1* | 7/2012 | Lubatschowski | A61F 9/008 606/4 |
| 2014/0066909 A1* | 3/2014 | Coleman | A61F 9/00827 606/5 |
| 2014/0378955 A1* | 12/2014 | Gray | A61F 9/00838 606/5 |
| 2015/0032091 A1* | 1/2015 | Teuma | A61F 9/00827 606/5 |
| 2015/0313756 A1* | 11/2015 | Skerl | A61F 9/009 606/4 |
| 2016/0059032 A1* | 3/2016 | Skerl | A61F 9/0008 604/20 |
| 2016/0095752 A1 | 4/2016 | Srinivasan | |
| 2016/0236006 A1* | 8/2016 | Donitzky | A61N 5/062 |
| 2016/0302971 A1* | 10/2016 | Morley | G16H 40/20 |
| 2017/0290703 A1* | 10/2017 | Teuma | A61F 9/013 |
| 2018/0085256 A1 | 3/2018 | Gray | |
| 2018/0243082 A1* | 8/2018 | Zheleznyak | A61F 2/1654 |
| 2020/0113736 A1* | 4/2020 | Bos | A61F 9/0079 |

* cited by examiner

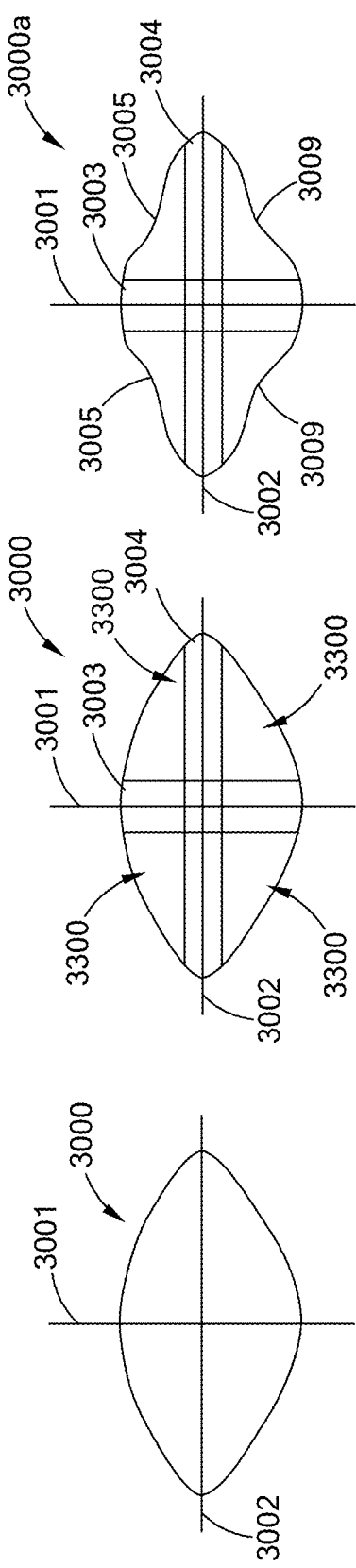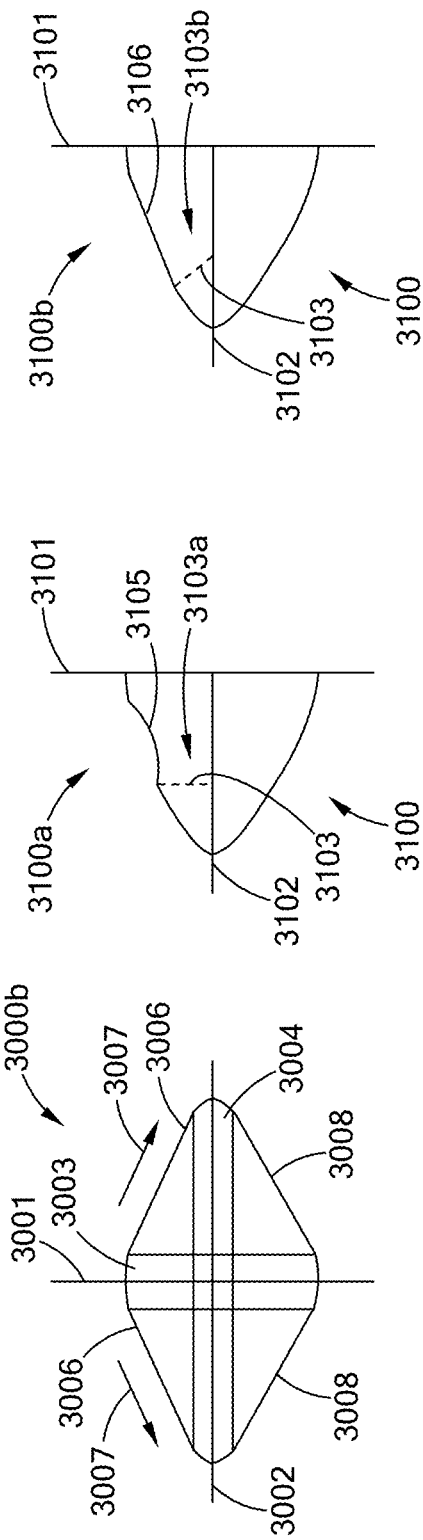

LASER METHODS AND SYSTEMS FOR ADDRESSING, MITIGATING AND REVERSING PRESBYOPIA

This application claims under 35 U.S.C. § 119(e)(1) the benefit of the filing date of U.S. provisional application Ser. No. 62/637,452, filed Mar. 2, 2018, the entire disclosure of which is incorporated herein by reference.

BACKGROUND OF THE INVENTION

Field of the Invention

The present invention relates to systems and methods for treating the structure of the natural human crystalline lens with a laser to address a variety of medical conditions, such as presbyopia and refractive error. In particular, embodiments of the present inventions relate to systems, methods and laser delivery patterns that improve the optical system of the eye and thus improve vision, provide a perceived or apparent improvement in vision and thus improve vision, and both.

Parlor tricks and optical illusions, creating perceived images in the brain, and thus apparent images that the individual actually sees, based on the way in which the brain processes images from the optical systems of the human eye have been known. For example, placing a small tube of paper in front of one eye and then your hand in front of the other eye, will create a perceived or apparent image of your hand with a hole in it. It is theorized that the brain combines these two images from the eye into one. Similarly, the use of mirror therapy for amputees uses a perceived image to affect the brain's function, thus the body's function. Mirror therapy is a form of motor imagery in which a mirror is used to convey visual stimuli to the brain through observation of one's unaffected body part as it carries out a set of movements. The underlying principle is that movement of the affected limb can be stimulated via visual cues originating from the opposite side of the body, but which when viewed as a mirror image, are perceived as being the afflicted limb. Hence, it is thought that this form of therapy can prove useful in patients who have lost movement of an arm or leg including those who have had a stroke, as well as, in relieving phantom pain.

In the present field of the inventions—ophthalmology, and laser systems to improve vision and threat conditions of the human eye—the techniques of "tricking" the brain into seeing better, have found limited application. One common utilization of this is what can be called mono-vision, where a user has two different contacts, or laser corrections, one for distance and one for near vision. The brain in about ⅓ of patients will readily combine and adjust the images, giving the patient the ability to see both near and far images.

The anatomical structures of the eye are shown in general in FIG. 8, which is a cross sectional view of the eye. The sclera 131 is the white tissue that surrounds the lens 103 except at the cornea 101. The cornea 101 is the transparent tissue that comprises the exterior surface of the eye through which light first enters the eye. The iris 102 is a colored, contractible membrane that controls the amount of light entering the eye by changing the size of the circular aperture at its center (the pupil). The ocular or natural crystalline lens 103, a more detailed picture of which is shown in FIG. 8A, (utilizing similar reference numbers for similar structures) is located just posterior to the iris 102. The terms ocular lens, natural crystalline lens, natural lens, natural human crystalline lens, and lens (when referring to the prior terms) are used interchangeably herein and refer to the same anatomical structure of the human eye.

Generally, the ocular lens changes shape through the action of the ciliary muscle 108 to allow for focusing of a visual image. A neural feedback mechanism from the brain allows the ciliary muscle 108, acting through the attachment of the zonules 111, to change the shape of the ocular lens. Generally, sight occurs when light enters the eye through the cornea 101 and pupil, then proceeds through the ocular lens 103 through the vitreous 110 along the visual axis 104, strikes the retina 105 at the back of the eye, forming an image at the macula 106 that is transferred by the optic nerve 107 to the brain. The space between the cornea 101 and the retina 105 is filled with a liquid called the aqueous 117 in the anterior chamber 109 and the vitreous 110, a gel-like clear substance, in the chamber posterior to the lens.

FIG. 8A illustrates, in general, components of and related to the lens 103 for a typical 50-year old individual. The lens 103 is a multi-structural system. The lens 103 structure includes a cortex 113, and a nucleus 129, and a lens capsule 114. The capsule 114 is an outer membrane that envelopes the other interior structures of the lens. The lens epithelium 123 forms at the lens equatorial 121 generating ribbon-like cells or fibrils that grow anteriorly and posteriorly around the ocular lens. The nucleus 129 is formed from successive additions of the cortex 113 to the nuclear regions. The continuum of layers in the lens, including the nucleus 129, can be characterized into several layers, nuclei or nuclear regions. These layers include an embryonic nucleus 122, a fetal nucleus 130, both of which develop in the womb, an infantile nucleus 124, which develops from birth through four years for an average of about three years, an adolescent nucleus 126, which develops from about four years until puberty which averages about 12 years, and the adult nucleus 128, which develops at about 18 years and beyond.

The embryonic nucleus 122 is about 0.5 mm in equatorial diameter (width) and 0.425 mm in Anterior-Posterior axis 104 (AP axis) diameter (thickness). The fetal nucleus 130 is about 6.0 mm in equatorial diameter and 3.0 mm in AP axis 104 diameter. The infantile nucleus 124 is about 7.2 mm in equatorial diameter and 3.6 mm in AP axis 104 diameter. The adolescent nucleus 126 is about 9.0 mm in equatorial diameter and 4.5 mm in AP axis 104 diameter. The adult nucleus 128 at about age 36 is about 9.6 mm in equatorial diameter and 4.8 mm in AP axis 104 diameter. These are all average values for a typical adult human lens approximately age 50 in the accommodated state, ex vivo. Thus this lens (nucleus and cortex) is about 9.8 mm in equatorial diameter and 4.9 mm in AP axis 104 diameter. Thus, the structure of the lens is layered or nested, with the oldest layers and oldest cells towards the center.

The lens is a biconvex shape as shown in FIGS. 8 and 8A. The anterior and posterior sides of the lens have different curvatures and the cortex and the different nuclei in general follow those curvatures. Thus, the lens can be viewed as essentially a stratified structure that is asymmetrical along the equatorial axis and consisting of long crescent fiber cells arranged end to end to form essentially concentric or nested shells. The ends of these cells align to form suture lines in the central and paracentral areas both anteriorly and posteriorly. The older tissue in both the cortex and nucleus has reduced cellular function, having lost their cell nuclei and other organelles several months after cell formation.

Compaction of the lens occurs with aging. The number of lens fibers that grow each year is relatively constant throughout life. However, the size of the lens does not become as large as expected from new fiber growth. The lens grows from birth through age 3, from 6 mm to 7.2 mm or 20% growth in only 3 years. Then the next approximate decade, growth is from 7.2 mm to 9 mm or 25%; however, this is over a 3 times longer period of 9 years. Over the next approximate 2 decades, from age 12 to age 36 the lens grows from 9 mm to 9.6 mm or 6.7% growth in 24 years, showing a dramatically slowing observed growth rate, while we believe there is a relatively constant rate of fiber growth during this period. Finally, in the last approximately 2 decades described, from age 36 to age 54, the lens grows by a tiny fraction of its youthful growth, from 9.6 to 9.8 mm or 2.1% in 18 years. Although there is a geometry effect of needing more lens fibers to fill larger outer shells, the size of the older lens is considerably smaller than predicted by fiber growth rate models, which consider geometry effects. Fiber compaction including nuclear fiber compaction is thought to explain these observations.

In general, presbyopia is the loss of accommodative amplitude. In general, refractive error is typically due to variations in the axial length of the eye. Myopia is when the eye is too long resulting in the focus falling in front of the retina. Hyperopia is when the eye is too short resulting in the focus falling behind the retina. In general, cataracts are areas of opacification of the ocular lens which are sufficient to interfere with vision.

Presbyopia most often presents as a near vision deficiency, the inability to read small print, especially in dim lighting after about 40-45 years of age. Presbyopia, or the loss of accommodative amplitude with age, relates to the eyes inability to change the shape of the natural crystalline lens, which allows a person to change focus between far and near, and occurs in essentially 100% of the population. Accommodative amplitude has been shown to decline with age steadily through the fifth decade of life.

As used herein unless specified otherwise, the recitation of ranges of values herein is merely intended to serve as a shorthand method of referring individually to each separate value falling within the range. Unless otherwise indicated herein, each individual value within a range is incorporated into the specification as if it were individually recited herein.

Generally, the term "about" as used herein unless stated otherwise is meant to encompass a variance or range of ±10%, the experimental or instrument error associated with obtaining the stated value, and preferably the larger of these.

This Background of the Invention section is intended to introduce various aspects of the art, which may be associated with embodiments of the present inventions. Thus the forgoing discussion in this section provides a framework for better understanding the present inventions, and is not to be viewed as an admission of prior art.

SUMMARY

There has existed a long standing and unfulfilled need to address presbyopia, replace the need for bifocals, and restore the ability to simultaneously have good near and far vision in older and presbyopic patients. The present inventions, among other things, solve these and other needs by providing the articles of manufacture, devices and processes set forth in this specification, drawings and claims.

Thus, there is provided a laser system for performing a laser operation to increase the amplitude of accommodation of an eye, the laser system having: a laser for generating a laser beam; a control system, the control system having a laser beam delivery pattern and configured to deliver the laser beam to a lens of an eye in the laser delivery pattern; and, the laser beam delivery pattern having an annular ring, located below the lens capsule and entirely within the lens; wherein the laser beam delivery pattern avoids contact with an AP pillar of lens material and an equatorial pillar of lens material; whereby after delivery of the laser beam pattern an AP pillar and an equatorial pillar of laser unaffected lens material remains; whereby after delivery of the laser beam pattern an annular shape changing zone is created within the lens and extends to and includes the lens capsule.

There is further provided these systems and methods having one or more of the following features: wherein the laser beam delivery pattern has a second annular ring; wherein the laser beam delivery pattern has a second annular ring; wherein the annular rings follow a shape of the lens capsule, and wherein the annular rings do not contact an equatorial axis of the lens; wherein the laser beam delivery pattern has a plurality of shots having a predetermined power density at the lens capsule and within the lens; and wherein the AP pillar has a cross sectional diameter of about 1 mm to about 2 mm; wherein the laser beam delivery pattern has a plurality of shots, wherein the laser shots have a pulse length, and a spot size at the focal point; and wherein the AP pillar defines an axis; and the AP pillar axis is coaxial with an AP axis of the eye; wherein the laser beam delivery pattern has a plurality of shots, wherein the laser shots have a pulse length, and a spot size at the focal point; and wherein the AP pillar defines an axis; and the AP pillar axis is not coaxial with an AP axis of the eye; wherein the AP pillar defines an axis; and the AP pillar axis is not coaxial and is titled with an AP axis of the eye; wherein the laser beam delivery pattern has a second annular ring; and wherein the AP pillar defines an axis; and the AP pillar axis is not coaxial with an AP axis of the eye; and, wherein the laser beam delivery pattern has a second annular ring; wherein the annular rings follow a shape of the lens capsule, and wherein the annular rings do not contact an equatorial axis of the lens; and wherein the AP pillar defines an axis; and the AP pillar axis is not coaxial and is titled with an AP axis of the eye.

Yet further there is provided a laser system for performing a laser operation to increase the amplitude of accommodation of an eye, the laser system having: a laser for generating a laser beam; a control system, the control system having a laser beam delivery pattern and configured to deliver the laser beam to a lens of an eye in the laser delivery pattern; and, the laser beam delivery pattern having an annular ring, located below the lens capsule and entirely within the lens; wherein the laser beam delivery pattern avoids contact with an AP pillar of lens material and an equatorial pillar of lens material; whereby after delivery of the laser beam pattern an AP pillar and an equatorial pillar of laser unaffected lens material remains; whereby after delivery of the laser beam pattern an annular shape changing zone is created within the lens and extends to and includes the lens capsule; whereby the annular ring defines a volume of lens material of about 4.0 mm$^3$ to about 75 mm$^3$; and a surface area to volume ratio of about 2 to about 5.

Still further there is provided these systems and methods having one or more of the following features: wherein the volume is from about 20 mm$^3$ to about 40 mm$^3$; wherein the surface area to volume ratio is about 3 to about 4; and wherein all of the laser beams in the laser beam shot pattern are below LIOB at the lens capsule.

Additionally, there is provided a method of creating structures within in the lens of an eye, the method having: delivering a laser beam in a laser beam delivery pattern to the lens of an eye; the laser beam delivery pattern having an annular ring, located below the lens capsule and entirely within the lens; wherein the laser beam delivery pattern avoids contact with an AP pillar of lens material and an equatorial pillar of lens material; wherein the laser beam is below LIOB at the lens capsule, whereby the lens capsule is not cut; the laser beam creating structures in the lens having an AP pillar, an equatorial pillar, and an annular shape changing zone having laser affected lens material and the lens capsule.

Still further there is provided these systems and methods having one or more of the following features: wherein the structures provide an increase in the effective depth of focus that is greater than the depth of focus based upon wave front analysis; wherein the increase is at least 1 diopter; wherein the increase is at least 2 diopters; wherein the increase is at least 3 diopters; wherein the annular shape changing zone defines a volume lens material of about 4.0 mm$^3$ to about 75 mm$^3$; wherein the annular shape changing zone defines a surface area to volume ratio of about 2 to about 5; wherein the annular shape changing zone defines a volume lens material of about 4.0 mm$^3$ to about 75 mm$^3$; and a surface area to volume ratio of about 2 to about 5; wherein the laser beam is below LIOB within 0.05 mm of the lens capsule; wherein the laser beam is below LIOB within 0.25 mm of the lens capsule; and wherein the laser beam is below LIOB within 0.5 mm of the lens capsule.

Moreover there is provided a method of enhancing vision with a laser beam delivery system, the method having: delivering a laser beam to an eye of a patient in a laser beam pattern from a laser beam laser beam delivery system; the eye having a lens having a lens and zonules; the lens having a lens capsule and lens material within the lens capsule; the eye having a first amplitude of accommodation; delivering the laser beam to the lens of the eye without cutting damaging, or weakening the lens capsule; and without cutting, damaging or weakening an AP pillar and an equatorial pillar of the lens material; wherein the laser beam forms a shape changing zone; whereby upon action of the zonules, the shape changing zone moves from a first shape to a second shape increasing the first amplitude of accommodation to a second amplitude of accommodation.

Still further there is provided these systems and methods having one or more of the following features: wherein the second amplitude of accommodation is from 0.05 diopters to 5 diopters; wherein the second amplitude of accommodation is from 1 diopter to 5 diopters; wherein the second amplitude of accommodation is greater than 2 diopters; wherein the second shape is concave; wherein the second shape essentially follows the shape of the lens; wherein the laser beam is below LIOB in the lens capsule; and wherein the laser beam never exceeds LIOB in the lens capsule, the AP pillar and the equatorial pillar.

Further there is provided a method of enhancing the vision of a patient, using a laser beam delivery system, the method having: positioning a patient with respect to a laser beam delivery system; the patient having in an eye; having a lens having a lens capsule and lens material within the lens capsule; delivering the laser beam to the lens of the eye without cutting damaging, or weakening the lens capsule; and without cutting, damaging or weakening an AP pillar and an equatorial pillar of the lens material; wherein the laser beam forms a shape changing zone; the shape changing zone capable of movement from a first shape to a second shape, thereby providing an amplitude of accommodation.

Still further there is provided these systems and methods having one or more of the following features: wherein the laser beam does not exceed LIOB in the lens capsule; wherein the laser beam does not exceed LIOB in the lens capsule and the AP pillar; wherein the laser beam does not exceed LIOB in the lens capsule, the AP pillar and the equatorial pillar; wherein the laser beam delivery pattern has a second annular ring; wherein the laser beam delivery pattern has a second annular ring; wherein the annular rings follow a shape of the lens capsule, and wherein the annular rings do not contact an equatorial axis of the lens; wherein the AP pillar has a cross sectional diameter of about 1 mm to about 2 mm; wherein the AP pillar defines an axis; and the AP pillar axis is coaxial with an AP axis of the eye; wherein the AP pillar defines an axis; and the AP pillar axis is not coaxial with an AP axis of the eye; wherein the AP pillar defines an axis; and the AP pillar axis is not coaxial and is titled with an AP axis of the eye; wherein the laser beam delivery pattern has a second annular ring; and wherein the AP pillar defines an axis; and the AP pillar axis is not coaxial with an AP axis of the eye; and, wherein the laser beam delivery pattern has a second annular ring; wherein the annular rings follow a shape of the lens capsule, and wherein the annular rings do not contact an equatorial axis of the lens; and wherein the AP pillar defines an axis; and the AP pillar axis is not coaxial and is titled with an AP axis of the eye.

BRIEF DESCRIPTION OF THE DRAWINGS

FIGS. 1A to 1D are cross sectional schematics of an embodiment of a laser process and laser patterns in accordance with the present inventions.

FIG. 2A to 2B are cross sectional schematics of an embodiment of a laser process and laser patterns in accordance with the present inventions.

DESCRIPTION OF THE PREFERRED EMBODIMENTS

Figure 1E:
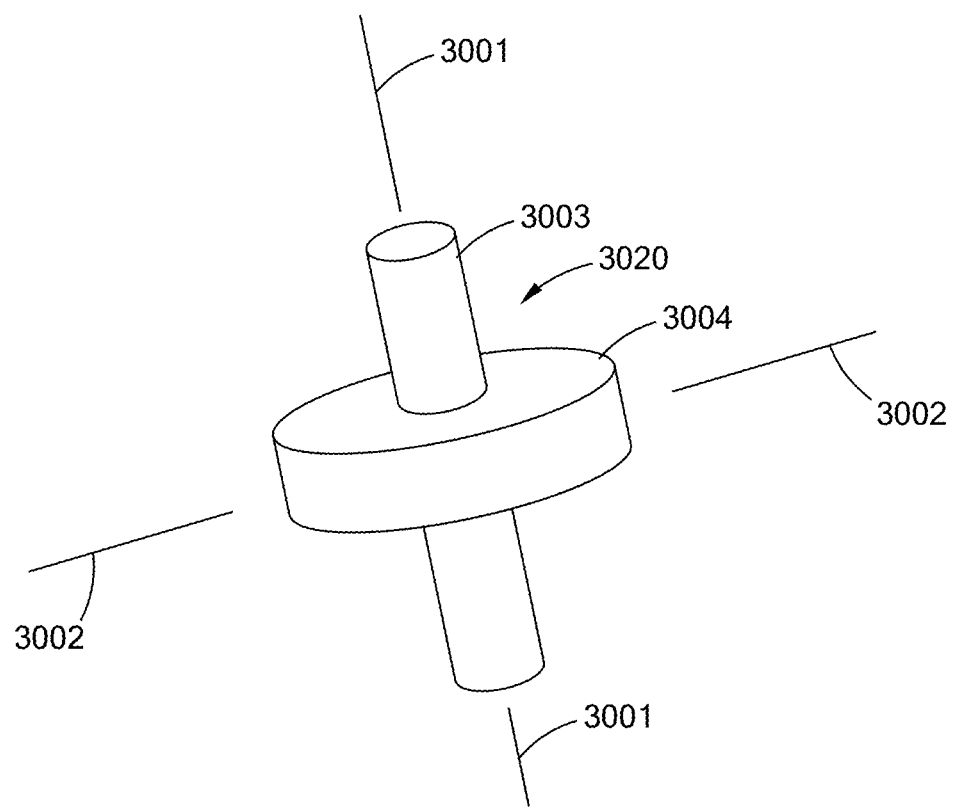
FIG. 1E is a perspective schematic of an embodiment of an unaffected section of a lens of an eye in accordance with the present inventions.

In general, embodiments of the present inventions provide systems and methods for addressing conditions of the natural crystalline lens of the eye, and in particular for delivering laser beam patterns to the eye to address, mitigate and reverse these conditions.

In general, embodiments of the present inventions relate to systems, methods and laser delivery patterns, contained within and provided by those systems, that when delivered to the lens of the eye will improve the optical system of the eye, and thus improve vision, provide a perceived or apparent improvement in vision and thus improve vision, and both. In particular, embodiments of the systems and the laser patterns that they provide, change the internal structure of the lens, causing forces acting on, within or both, the lens to change the shape of the lens to provide, or improve, the patient's vision with greater accommodation. Thus, the actual, apparent or perceived, and both amplitude of accommodation of the patient is greatly improved, having the ability to perceive 2-7 diopters, 3-5 diopters, 3 diopters, 4 diopters, 5 diopters, 6 diopters and more amplitude of accommodation, greater lesser amounts and amounts within these ranges are contemplated. Thus, using Hofstetter's average amplitude of accommodation formula based on age (amplitude of accommodation=18.5−(0.3*age in years)) embodiments of the present laser systems can return the vision of a 55-year old to the vision of a 50-year old, the vision of a 45-year old, the vision of a 40-year old, the vision of a 35-year old and younger. Thus, these systems and methods have the ability to in effective reverse, and reverse, the effects of presbyopia by 5 to 25 years, 5 years or more, 10 years or more, 15 years or more, and 20 years or more.

Turning to FIG. 1A to 1D there is provided a cross section of a lens that has an embodiment of a laser pattern delivered to the lens to define an embodiment of an internal structure. These figures then illustrate the delivery of the laser pattern, and its effects on the amplitude of accommodation of the lens. Thus, in FIG. 1A there is provided a lens 3000 having an AP axis 3001 and an equatorial axis 3002. In FIG. 1B a laser treatment pattern 3300 is delivered to the lens, which does not shoot a center area along the AP axis 3001, which defines an AP pillar structure 3003 (a pillar of material along and surrounding the AP axis where the laser beam is not delivered, does not ablate or remove material, does not affect the structural and optical properties of the AP pillar, and preferably all of these). The laser treatment pattern 3300 also does not shoot a center area along the equatorial axis 3002, which defines an equatorial pillar structure 3004, which given the shape of the lens is disk shaped. The laser treatment pattern weakens the lens material near the surface, and preferably below the surface of the lens capsule to a point adjacent the pillars 3003, 3004.

Turning to FIG. 1C shows the laser treated lens, and internal pillar structures 3003, 3004 when the lens is in an accommodated state 3000*a*. Thus, the accommodated lens 3000*a* has indentations or depressions (which would be annular in this embodiment), one indentation 3005 forming in the anterior side, and the other indentation 3009 forming in the posterior side. Turning to FIG. 1D, when the lens is in a disaccommodated state 3000*b*, the zonules are exerting forces on the eye, generally depicted as arrows 3007. Thus, the indentations flatten out as taut annular areas 3006, 3008. Thus, comparing the shape of the accommodated lens 3000*a* to the disaccommodated lens 3000*b*, the change in the lens providing of increased accommodative amplitude (over the untreated lens) is illustrated.

Turning to FIG. 1E, there is shown the internal support structure 3020, in isolation from the lens, for illustration purposes (noting that this internal structure in practice would not be removed from the lens). The internal support structure has the AP pillar 3003 and the equatorial pillar 3004, which form the integral internal support structure 3020.

In the embodiment of FIG. 1 A-D, the internal support structure has ends that extend out to and contact or include the lens capsule. The internal support structure is shown (in isolation from the lens material for the purposes of illustration in FIG. 1E). Thus, the AP pillar 3003 would have an anterior end at the anterior lens capsule and a posterior end at the posterior lens capsule. Similarly, in this embodiment, the equatorial pillar 3004, which although called a pillar, is a disc shape, would have an end along the equator of the lens capsule. Thus, it can be seen that the regions of accommodation, e.g., 3005-3006, and 3009-3008, are located between the ends of the pillars.

To further illustrate the mechanical theory believed to be occurring in the lens treated to provide for internal support structures one can turn to FIGS. 2A and 2B. FIG. 2A is a schematic cross section of a portion of a lens 3100 in an accommodated state 3100*a*, having an indent 3105. (As discussed in further detail below, the indent 3105 corresponds to, or is, a shape changing zone that is formed by the delivery of the laser pattern and the pillars.) FIG. 2B is a schematic cross section of a portion of the lens 3100 in a disaccommodated state 3100*b*, having taut section 3106. The AP axis 3101 and a portion of the equatorial axis 3102 are shown for reference. To further explain the operation of the accommodation of the lens one can envision a beam 3103 in the lens 3100. As the zonules exert a force the beam is moved from its first position 3103*a* (accommodated) to its second position 3103*b* (disaccommodated). In moving from the first position 3103*a* to the second 3103*b* the lens capsule is drawn tight, creating the taut area 3016, where the indent 3105 had been.

During accommodation, in embodiments, the beam 3103 can have a change of about 5° in angle, about 10° in angle, about 20° in angle, about 30° in angle, about 40° in angle, about 50° in angle, about 45°, from 5° to about 50° change in angle, about 15° to about 40° change in angle, and larger and smaller changes as well as changes within these ranges.

Further, the present internal support structure based accommodation, provides the advantage that only a small amount of lens material has to move in order for their to be effective accommodation (e.g., the patient can notice the difference in focus, reading etc.). When accommodation is restored through changing large areas of the lens, and in particular areas along the AP axis, so that accommodation occurs by changing the entire shape of the lens along the AP axis (i.e., the whole lens flattens out, or increases in height), a large amount of lens material (in general substantially larger than with the use of internal support structures) must be moved to have an effective accommodation. The movement of a smaller amount (e.g., mass, volume and both) of lens materials enables faster accommodation.

Thus, after delivery of embodiments of the laser beam pattern, and the formation of embodiments of the axial and equatorial pillars, the volume of lens material that changes shape during accommodation is from about 10% to about 80%, from about 10% to about 50%, from about 5% to about 30%, from about 10% to about 40%, from about 5% to about 25%, less than 50%, less than 40%, less than 30%, and less than 20%. This volume of material that is treated by the laser shot pattern, and that changes shape during accommodation, is referred to as the "laser effected accommodation volume" of lens material, or for the area that changes shape, the "laser effected accommodation area" of lens tissue.

Figure 3:
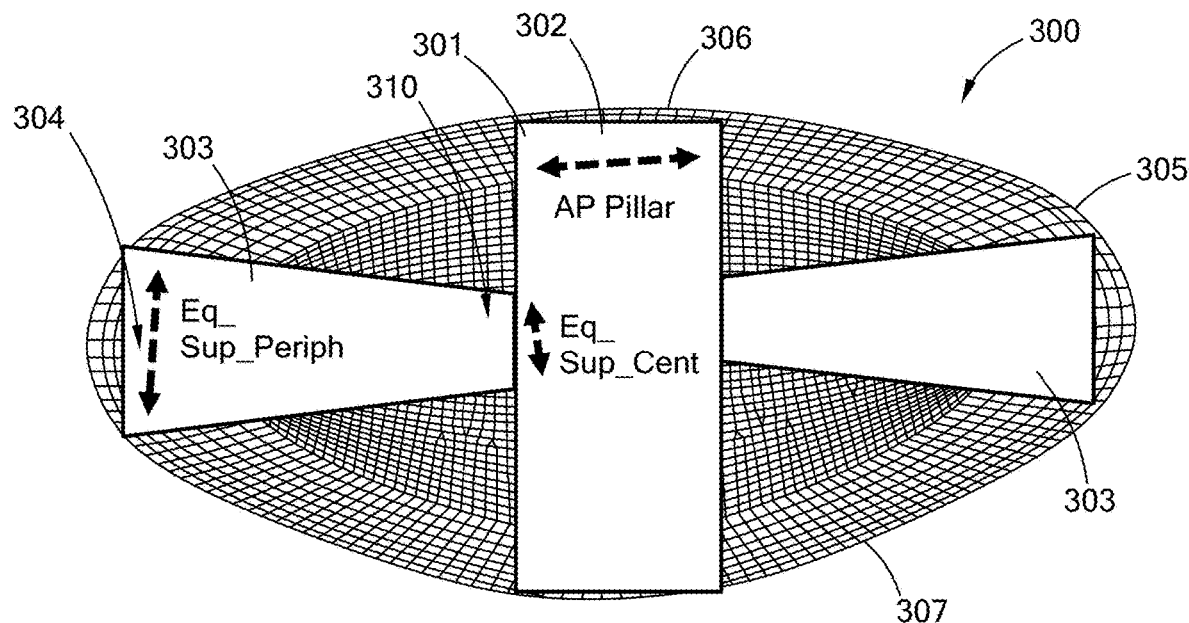
FIG. 3 is a cross sectional schematic of an embodiment of an AP pillar and equatorial pillar, in a lens of an eye, in accordance with the present inventions.

An embodiment of a laser delivery pattern for delivering a laser beams to the lens of the eye is shown in FIG. 3. The lens 300 has a laser delivery pattern delivered to the lens, leaving an AP pillar 301 that extends from the anterior lens capsule 306 to the posterior lens capsule 307, has a circular cross section with a diameter shown by arrow 302 (In these figures, it is noted that this diameter is the actual diameter of the pillar, i.e., normal to the pillar's axis; and not at some angle. It is noted that the arrows in these figures is only by way of illustration). The diameter can be from about 1 mm to about 3 mm, from about 1 mm to about 5 mm, and preferably the diameter is 2 mm, and preferably the center axis of the pillar 302 is coaxial with the AP axis of the lens. It being understood that the pillar axis can be off axis with the AP axis, that the pillar can have a varying diameter, and that the pillar cross section can be shapes other than circular, such as square, rectangular, bowling pin, and elliptical.

The equatorial pillar 303 is disc shaped and has a thickness 304 that is greater near the lens capsule 305, and thinner 310, where the pillar 303 joints the AP pillar 301. It being understood that in other embodiments the equatorial pillar can have a uniform thickness or have a greater thickness at the lens capsule; and vice versa. In the embodiment of FIG. 3, the equatorial pillar 303 has an axis that is on, coincident or co-planar with the equatorial axis (or central plane) of the lens. In embodiments the axis of the equatorial pillar can be above or below the center equatorial axis of the lens. The equatorial pillar can have thickness of from about 0.25 mm to about 2 mm, about 0.75 mm to about 3 mm, 0.25 mm to about 4 mm, more than ⅓ of the lens, all values within these ranges, and preferably about from 0.5 mm to 1 mm. Preferably the equatorial pillar is coincident with the lens equatorial axis. In embodiments, the equatorial pillar could also be placed anterior or posterior to the equatorial axis, or in the plane passing through half lens thickness.

Embodiments of the annular laser beam delivery patterns have a width (the distance from the inner edge of the ring, near the AP pillar, to outer edge of the ring near lens capsule) from about 1.5 mm to 3.5 mm, about 2.0 mm to about 3.0 mm, about 3 mm, about 2.5 mm, about 2 mm, about 2.0 mm to 2.9 mm, about 1 mm to about 4 mm, and greater and smaller widths, as well as, all widths within these ranges. The ring can have a maximum thickness (recognizing that in embodiments of the ring it may be uniform, thicker near the center of the ring's width, or thicker at one or both edges of the ring), which is from about 0.2 mm to about 1.5 mm, about 0.3 mm to about 1.0 mm, and greater and smaller maximum thickness, as well as, values within these ranges.

The volume of the laser beam delivery pattern can be from about 4.0 mm$^3$ to about 75 mm$^3$, about 10 mm$^3$ to about 50 mm$^3$, about 20 mm$^3$ to about 40 mm$^3$, about 25 mm$^3$, about 30 mm$^3$, about 40 mm$^3$ and about 50 mm$^3$ and greater and smaller areas, as well as, areas within these ranges. The laser beam delivery pattern can have a surface area to volume ratio ("sa/vol") of from about 2 to about 5, about 2.5, about 3, about 3.5, about 4, and about 4.5 mm$^3$ and greater and smaller sa/vol, as well as, sa/vol within these ranges. It being understood that when the laser beam delivery pattern has two annular rings, e.g., one above and one below the equatorial axis, the total volume will be the sum of each zone. The lens material that this struck by the laser beam pattern, will generally correspond with the volume of the laser beam delivery pattern.

In preferred embodiments, the lens material of the AP and equatorial pillars are not weakened, cut, or ablated by the laser beam delivery pattern. In preferred embodiments, the laser beam delivery pattern is not delivered into the pillars. The pillars are formed by, or can be viewed as the remaining material after delivery of the laser beam pattern that is not changed by the laser beam, and is structurally stronger than the laser treated material. The pillars essentially retain the original strength and other properties of the lens material, before delivery of the laser beam to the lens.

Figure 4:
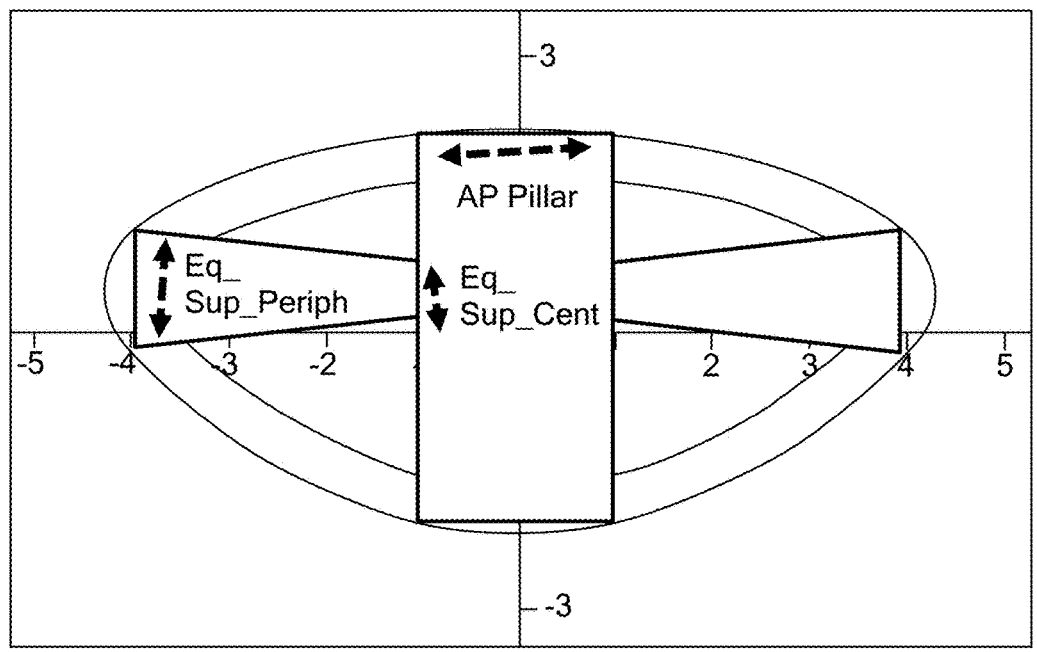
FIG. 4 is a cross sectional schematic of an AP pillar and equatorial pillar, in a lens of an eye, in accordance with the present inventions.

Turning to the embodiment of FIG. 4, the equatorial pillar is thinner than that of the embodiment of FIG. 3 and is above the equatorial axis for the lens.

Figure 5A:
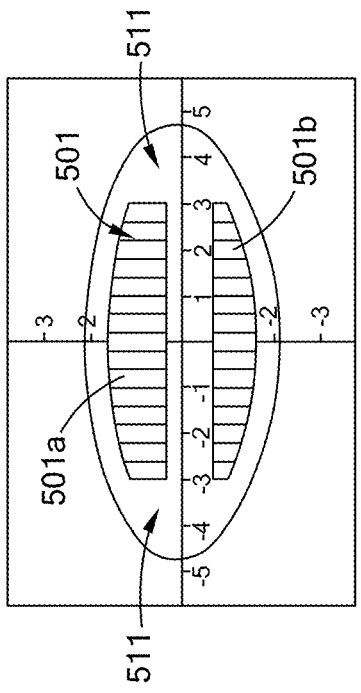
FIGS. 5A and 5C are cross sectional and perspective views, respectively, of an embodiment of a laser shot pattern in accordance with the present invention.
Figure 5B:
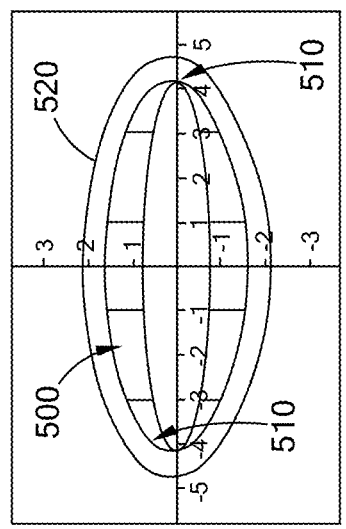
FIGS. 5B and 5D are cross sectional and perspective views, respectively, of an embodiment of a laser shot pattern in accordance with the present inventions.
Figure 5C:
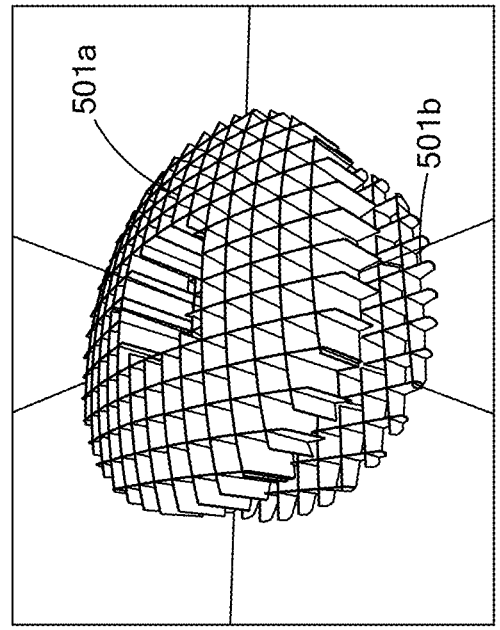

Turning to FIGS. 5A and 5C there is shown a cross sectional and perspective view of an embodiment of a laser beam delivery pattern 500. The laser beam delivery pattern 500 has uniform laser shots that form two discs, an upper 500a and a lower 500b. The pattern 500 follows, i.e., has the same shape as, the lens capsule 520. In this embodiment, the AP pillar would have a uniform diameter, and be circular. The equatorial pillar would be disc shaped, extending out from the AP pillar by 3 mm (−1 to −3 and 1 to 3 as shown on the x axis of the FIG. 5A). The surface of the equatorial pillar would have the same shape, i.e., the same curvature, as the lens. This laser delivery pattern would also provide for a third pillar, which would be a thickened ring that extends around, or on top of and below the equatorial pillar, generally in the area 510 of the lens.

Figure 5D:
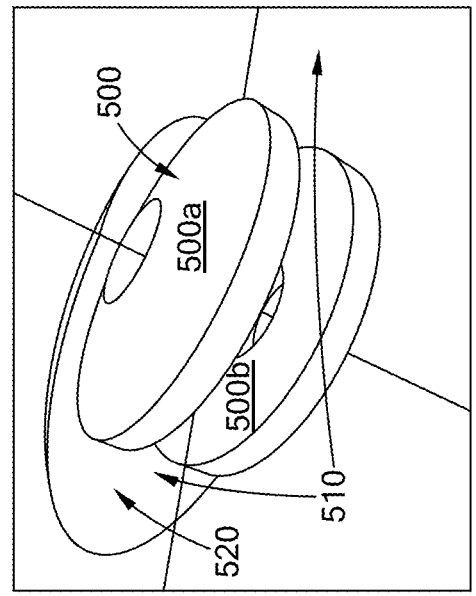

Turning to FIGS. 5B and 5D there is shown a cross sectional and perspective view of an embodiment of a laser beam delivery pattern 501. The laser beam delivery pattern has grid like shots that form two discs, an upper disc pattern 501a and a lower disc pattern 501b. In this embodiment, the pattern is made up of intersecting planes that form an "ice cube tray" like pattern, it being recognized that other patterns and arrangements of shots in a particular shot pattern can be used. The upper and lower curves of the pattern follow, i.e., has the same shape as, the lens capsule. In this embodiment, the AP pillar would have a uniform diameter, and be circular. The equatorial pillar would be disc shaped, extending out from the AP pillar by 3 mm (−1 to −3 and 1 to 3 as shown on the x axis of the FIG. 5S). The surfaces (top and bottom) of the equatorial pillar would be planar, i.e., they are flat, not curved, and do not follow the curvature of the lens. This laser delivery pattern would also provide for a third pillar, which would be a thickened ring that extends around, or on top of and below the equatorial pillar, generally in the area 511 of the lens.

Figure 9:
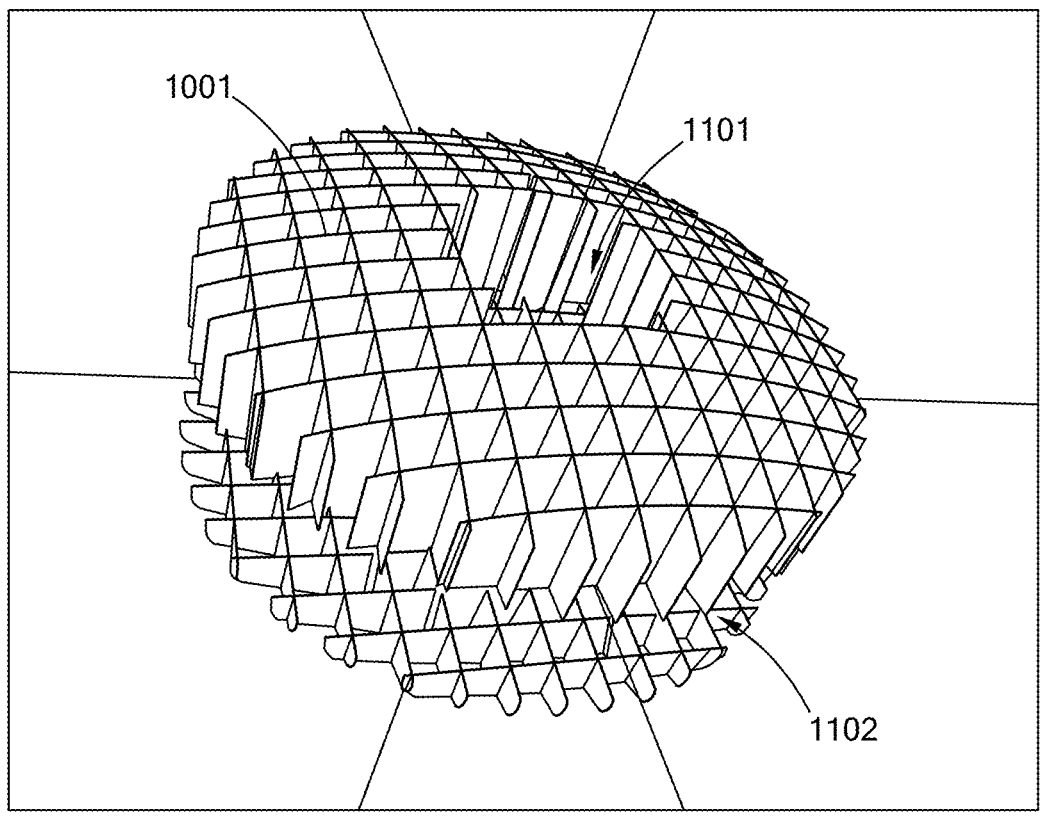
FIG. 9 is a perspective view of an embodiment of an off-axis laser shot pattern in accordance with the present inventions.
Figure 10:
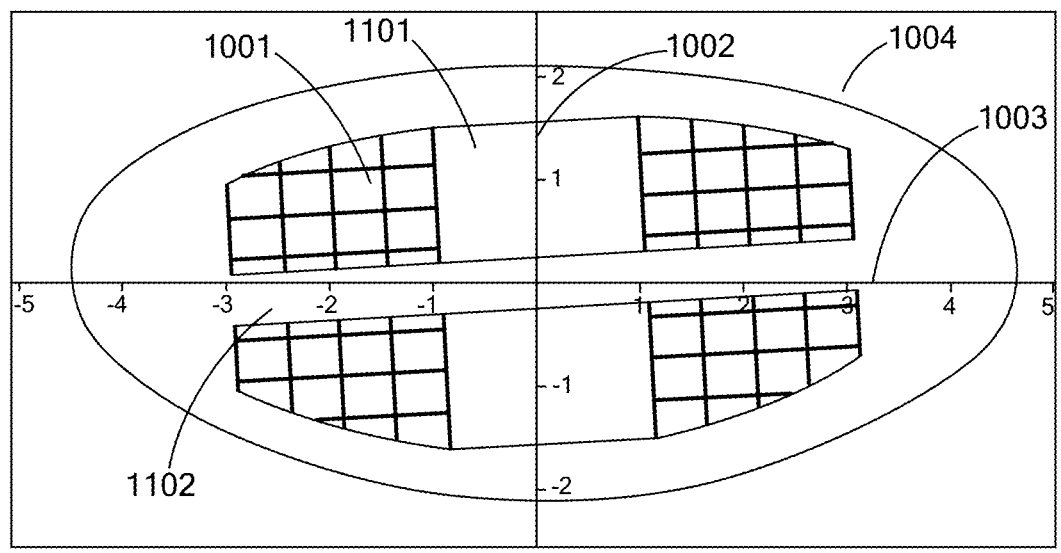
FIG. 10 is a cross sectional view of the laser shot pattern of FIG.

FIG. 9 is a perspective view of an off-axis laser beam delivery pattern 1001, which will provide an off-axis AP pillar 1101 and an off-axis equatorial pillar 1102. FIG. 10 is a cross section of the pattern of FIG. 9. FIG. 10 shows the off axis pattern 1001 with respect to the AP axis 1002, the equatorial axis 1003 and the lens capsule 1004.

In embodiments, the AP pillar can be off axis with the AP axis, the equatorial pillar can be off axis with the equatorial axis and both.

Thus, in embodiments of the present inventions, the delivery of the laser beam to the lens in embodiments of the laser beam patterns create, through leaving unaffected by the laser beam, the AP pillar and the equatorial pillars, these pillars in conjunction with the annular areas that have changing shape by the force of the zonules. These areas of changing shape are annular rings that go around the AP pillar and can be on the anterior side of the lens, the posterior side of the lens and preferably both sides of the lens. These areas of changing shape can transition from: (i) the curvature of the lens (pre-treatment), to (ii) essentially the same as the curvature of the lens (i.e., arcs of the curves are within at least 90% of each other), to (iii) straight, to (iv) concave. This transition is repeatable, can be performed forward (i) to (iv) and backward (iv) to (i), as well as combination of these, for example (ii) to (iii) to (i) to (iv) to (i).

The annular areas of changing shape have a width (the distance from the inner edge of the ring, near the AP pillar, to outer edge of the ring near lens capsule) from about 1.5 mm to 3.5 mm, about 2.0 mm to about 3.0 mm, about 3 mm, about 2.5 mm, about 2 mm, about 2.0 mm to 2.9 mm, and greater and smaller widths, as well as, widths within these ranges. The ring can have a maximum thickness (recognizing that in embodiments of the ring it may be uniform, thicker near the center of the ring's width, or thicker at one or both edges of the ring), which is from about 0.2 mm to about 1.5 mm, about 0.3 mm to about 1.0 mm, and greater and smaller maximum thickness, as well as, values within these ranges.

The volume of the annular area of changing shape, i.e. the "shape changing zone", can be from about 4.0 mm$^3$ to about 75 mm$^3$, about 10 mm$^3$ to about 50 mm$^3$, about 20 mm$^3$ to about 40 mm$^3$, about 25 mm$^3$, about 30 mm$^3$, about 40 mm$^3$ and about 50 mm$^3$ and greater and smaller areas, as well as, areas within these ranges. The shape changing zone can have a surface area to volume ratio ("sa/vol") of from about 2 to about 5, about 2.5, about 3, about 3.5, about 4, and about 4.5 mm$^3$ and greater and smaller sa/vol, as well as, sa/vol within these ranges. It being understood that when there are two shape changing zones, e.g., one above and one below the equatorial axis, the total volume will be the sum of each zone.

These volumes and sa/vol for the shape changing zone permit very rapid accommodation rate, i.e, the shape can be changed very quickly, an accommodation rate that is equal to an eye having no presbyopia (e.g., 14-20 year old eye), and rates equal to or superior to accommodating IOLs.

In preferred embodiments the delivery of the laser pattern is entirely within the lens, and passes through, and does not otherwise effect, cut or damage the lens capsule. Thus, the creation of the shape changing zone occurs without changing, e.g., damaging, cutting, the lens capsule with the laser. It being understood that the lens capsule is a part of the shape changing zone, and as such the shape changing zone has both laser affected and laser unaffected materials.

In embodiments, the accommodation that is provided from embodiments of application of the present patterns and laser treatments, can be totally a brain function, in which case there is no material in the lens that is actually moving. In this embodiment accommodation is exceeding fast, and faster than the rate of accommodation in a young eye, e.g., fully accommodative eye, where the lens is changing shape. In other embodiments where the lens shape or surface is dynamically changing, e.g., moving, the rate of accommodation is based primarily on the neurological loop controlling the zonules.

In embodiments of the present inventions delivery of the laser beam patterns and creation of the pillars and shape changing zones provides the added benefit of changing and increasing the "effective depth of focus" beyond the physical changes to the eye as an optical system. The "effective depth of focus", as used herein, is the depth of focus that the patient sees, as measured by conventional devices and techniques, such as, a refractor and Snellen Eye Chart. (Preferably, as determined by a licensed professional.)

In embodiments of the present inventions the effective depth of focus increases from about 0.5 to about 3 diopters, about 0.5 diopters, about 1 diopters, about 2 diopters, about 3 diopters, about 3.5 diopters, and greater and smaller values as well as values within these ranges over the physical changes to the eye, as an optical system. These increases are over, e.g., in addition to, the accommodation that the eye as a physical optical system is capable off based upon optical measuring systems such as wavefront analysis. Thus, for example, if after performing an embodiment of the present laser operations, the patient has an effective depth of focus of 5 diopters, and wave front analysis of the eye shows an accommodation of 3 diopters, the laser operation would have obtained a change, (here an increase) in the effective depth of focus of 2 diopters over the eye's optical system.

In this manner it is theorized that one result of embodiments of the present laser operations is for the eye to provide images (e.g., image signals) to the brain that are processed from the eye in a manner to that gives enhanced, e.g., better sight, than the optical improvements to the optical components, e.g., the lens with shape changing zone and pillars, alone could provide.

A further benefit of embodiments of the present inventions is that no hyperopic shift occurs. Thus, an approach that simply "softens" the lens material to restore accommodation would also cause the lens to be stretched radially by the zonular forces, inducing a flattening and consequential drop in lens optical power; this would manifest as a hyperopic shift in the subjects vision. By using pillars to add radial structural stability the hyperopic shift is reduced, minimized and preferably prevented.

Figure 11:
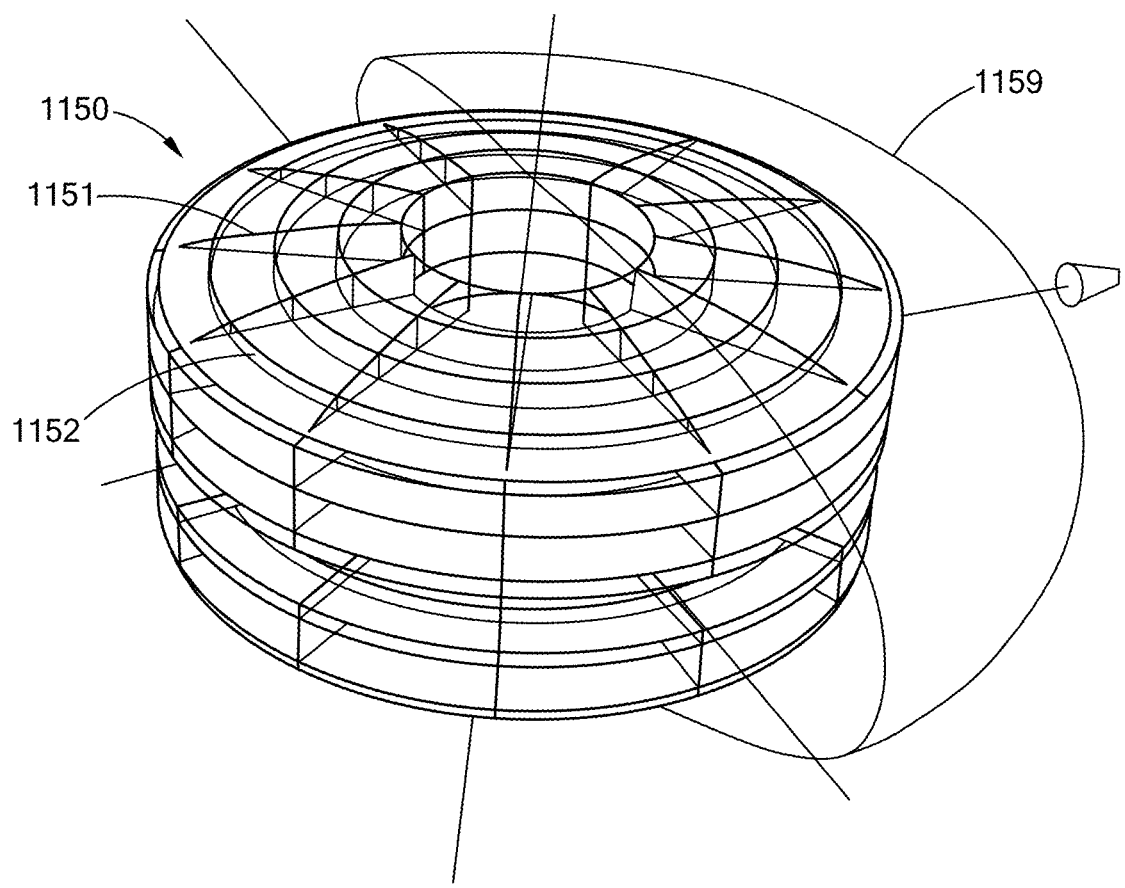
FIG. 11 is a perspective, partial cutaway view, of an embodiment of a laser shot pattern in the lens of the eye, in accordance with the present inventions.

FIG. 11 is a partial cutaway perspective view of the lens, showing an embodiment of a shot pattern to provide an AP pillar and an equatorial pillar. The laser shot pattern 1150 is shown in the lens, and with respect to a cutaway (for purposes of the figure) of the lens capsule 1159. The laser pattern 1150 has a series of radial cuts, e.g., 1151 and a series of concentric cuts, e.g., 1152.

Figure 12:
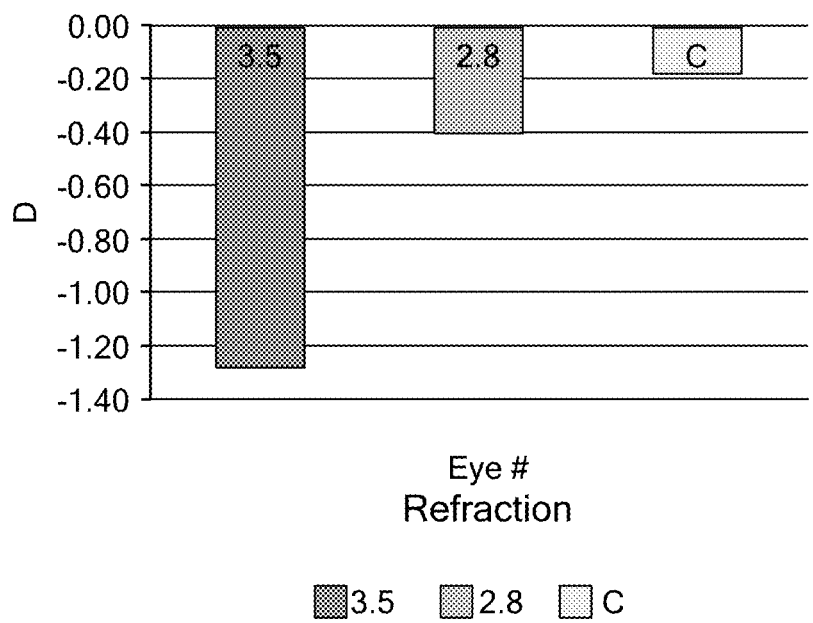
FIG. 12 is a chart showing near add refractive power for an embodiment of a laser operation using an embodiment of a laser shot pattern in accordance with the present inventions.

Turning to FIG. 12 there is shown a graph of the improvement in diopters that are obtained from a pattern of the type of FIG. 11, but without the radial cuts. D is a control. For the bar 2.8 a near add of −0.4 diopters is obtained. For the bar 3.5 a near add of −1.20 diopters is obtained. These measurements were obtained using wave front analysis.

Figure 13:
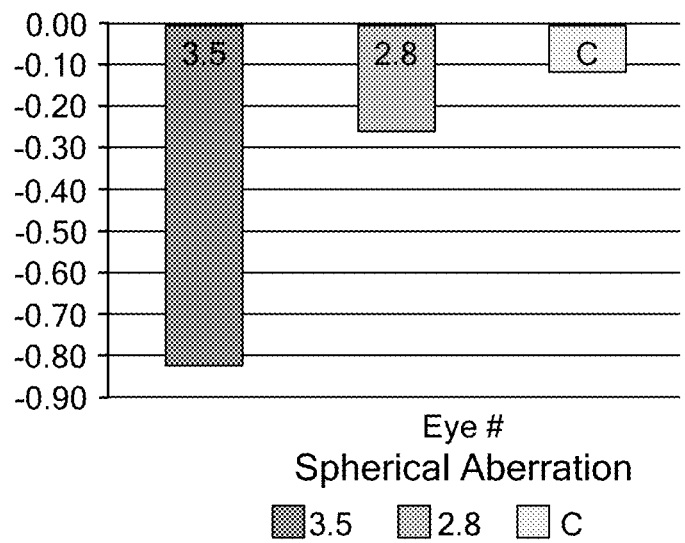
FIG. 13 is a chart showing increase of the negative spherical aberration for an embodiment of a laser operation using an embodiment of a laser shot pattern in accordance with the present inventions.

Turning to FIG. 13 there is shown a graph of the improvement in diopters that are obtained from a pattern of the type of FIG. 11 without the radial cuts. In this figure spherical aberration vs refraction is shown and analyzed. D is a control. For the bar 2.8 a spherical aberration increase of −0.25 diopters is obtained. For the bar 3.5 a spherical aberration increase of −0.80 diopters is obtained. These measurements were obtained using wave front analysis.

Figure 6:
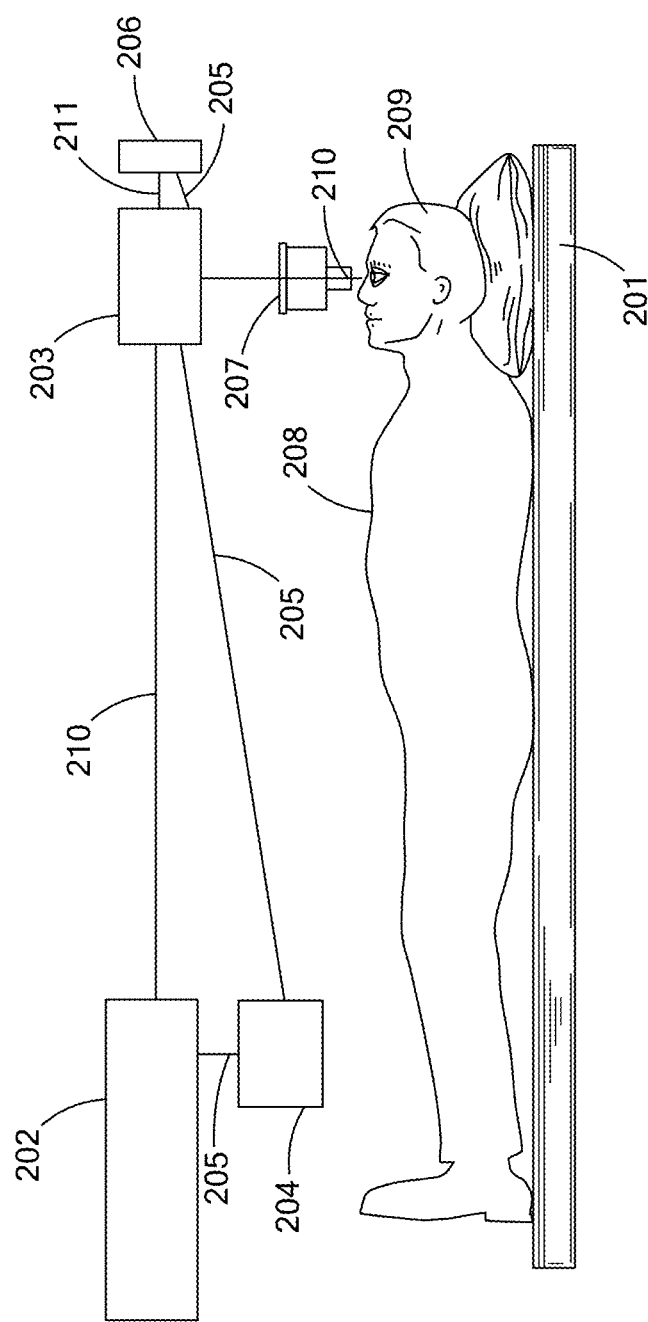
FIG. 6 is schematic view of an embodiment of a laser system in accordance with the present invention.
Figure 14:
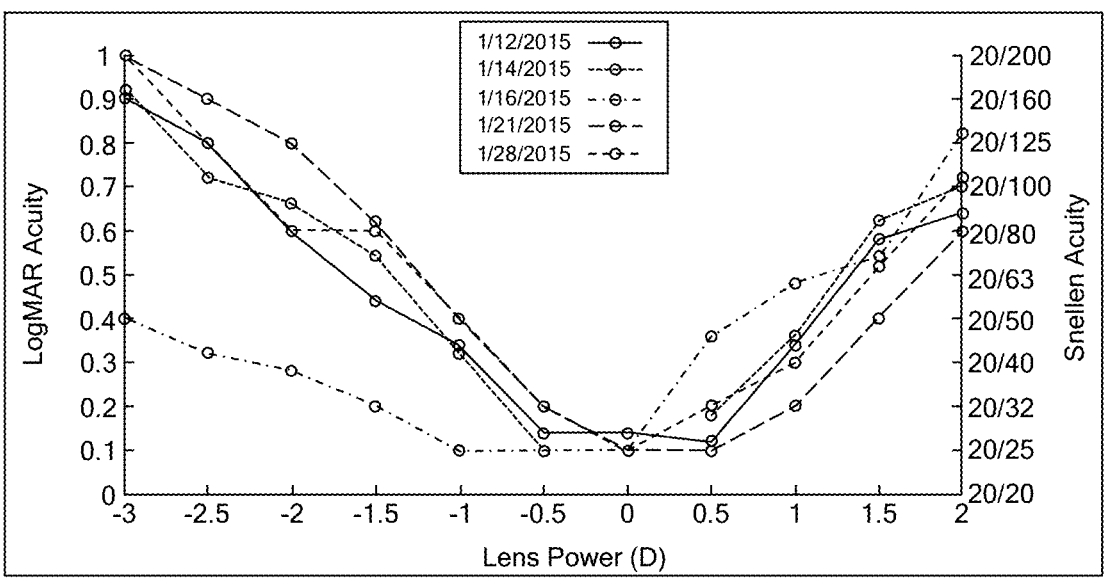
FIG. 14 is a chart showing defocus curves before and after laser treatment using embodiments of laser operations in accordance with the present inventions.

In FIG. 14 there is shown a chart of defocus curves before and after the laser treatment An embodiment of a laser system, having embodiments of the present laser patterns, for performing the laser procedures of the present inventions is generally shown in FIG. 6, where there is provided a system for delivering a laser beam shot pattern to the lens of an eye comprising: a patient support 201; a laser 202; optics for delivering the laser beam 203; a control system for delivering the laser beam to the lens in a particular pattern 204, which control system 204 is associated with and/or interfaces with the other components of the system as represented by lines 205; a means for determining the position of lens with respect to the laser 206, which means 206 receives an image 211 of the lens of the eye; and a laser patient interface 207.

The patient support 201 positions the patient's body 208 and head 209 to interface with the optics for delivering the laser beam 203.

In general, the laser 202 should provide a beam 210 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers would include: the Delmar Photonics Inc. Trestles-20, which is a Titanium Sapphire (Ti:Sapphire) oscillator having a wavelength range of 780 to 840 nm, less than a 20 femtosecond pulse width, about 100 MHz PRF, with 2.5 nanojoules; the Clark CPA-2161, which is an amplified Ti:Sapphire having a wavelength of 775 nm, less than a 150 femtosecond pulse width, about 3 KHz PRF, with 850 microjoules; the IMRA FCPA (fiber chirped pulse amplification) pjewel D series D-400-HR, which is a Yb:fiber oscillator/amplifier having a wavelength of 1045 nm, less than a 1 picosecond pulse width, about 5 MHz PRF, with 100 nanojoules; the Lumera Staccato, which is a Nd:YVO4 having a wavelength of 1064 nm, about 10 picosecond pulse width, about 100 KHz PRF, with 100 microjoules; and, the Lumera Rapid, which is a ND:YVO4 having a wavelength of 1064 nm, about 10 picosecond pulse width, and can include one or more amplifiers to achieve approximately 2.5 to 10 watts average power at a PRF of between 25 kHz to 650 kHz and also includes a multi-pulsing capability that can gate two separate 50 MHz pulse trains. and, the IMRA FCPA (fiber chirped pulse amplification) pJewel D series D-400-NC, which is a Yb:fiber oscillator/amplifier having a wavelength of 1045 nm, less than a 100 picosecond pulse width, about 200 KHz PRF, with 4 microjoules. Thus, these and other similar lasers may be used as therapeutic lasers.

In general, the optics for delivering the laser beam 203 to the natural lens of the eye should be capable of providing a series of shots to the natural lens in a precise and predetermined pattern in the x, y and z dimension. The optics should also provide a predetermined beam spot size to cause photodisruption with the laser energy reaching the natural lens. Thus, the optics may include, without limitation: an x y scanner; a z focusing device; and, focusing optics. The focusing optics may be conventional focusing optics, and/or flat field optics and/or telecentric optics, each having corresponding computer controlled focusing, such that calibration in x, y, z dimensions is achieved. For example, an x y scanner may be a pair of closed loop galvanometers with position detector feedback. Examples of such x y scanners would be the Cambridge Technology Inc. Model 6450, the SCANLAB hurrySCAN and the AGRES Rhino Scanner. Examples of such z focusing devices would be the Phsyik International Peizo focus unit Model ESee Z focus control and the SCAN LAB varrioSCAN.

In general, the control system for delivering the laser beam 204 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system as well as maintaining data, obtaining data and performing calculations. Thus, the control system may contain the programs that direct the laser through one or more laser shot patterns.

In general, the means for determining the position of the lens with respect to the laser 206 should be capable of determining the relative distance with respect to the laser and portions of the lens, which distance is maintained constant by the patient interface 207. Thus, this component will provide the ability to determine the position of the lens with respect to the scanning coordinates in all three dimensions. This may be accomplished by several methods and apparatus. For example, x y centration of the lens may be accomplished by observing the lens through a co-boresighed camera system and display or by using direct view optics and then manually positioning the patients' eye to a known center. The z position may then be determined by a range measurement device utilizing optical triangulation or laser and ccd system, such as the Micro-Epsilon opto NCDT 1401 laser sensor and/or the Aculux Laser Ranger LR2-22. The use of a 3-dimensional viewing and measurement apparatus may also be used to determine the x, y and z positions of the lens. For example, the Hawk 3 axis non-contact measurement system from Vision Engineering could be used to make these determinations. Yet a further example of an apparatus that can be used to determine the position of the lens is a 3-dimension measurement apparatus. This apparatus would comprise a camera, which can view a reference and the natural lens, and would also include a light source to illuminate the natural lens. Such light source could be a structured light source, such as for example a slit illumination designed to generate 3-dimensional information based upon geometry. Further one, two, three, four or more, light sources can be positioned around the eye and the electronically activated to provide multiple views, planar images, of the eye, and in particular the cornea and the lens, at multiple planar slices that can them be integrated to provide data for position and location information relative to the laser system about those structures.

A further component of the system is the laser patient interface 207. This interface should provide that the x, y, z position between the natural lens and the laser remains fixed during the procedure, which includes both the measurement steps of determining the x y z position and the delivery step of delivering the laser to the lens in a shot pattern. The interface device may contain an optically transparent applanator. One example of this interface is a suction ring applanator that is fixed against the outer surface of the eye and is then positioned against the laser optical housing, thus fixing the distance between the laser, the eye and the natural lens. Reference marks for the 3-dimensional viewing and measuring apparatus may also be placed on this applanator. Moreover, the interface between the lower surface of the applanator and the cornea may be observable and such observation may function as a reference. A further example of a laser patient interface is a device having a lower ring, which has suction capability for affixing the interface to the eye. The interface further has a flat bottom, which presses against the eye flattening the eye's shape. This flat bottom is constructed of material that transmits the laser beam and also preferably, although not necessarily, transmits optical images of the eye within the visible light spectrum. The upper ring has a structure for engaging with the housing for the laser optics and/or some structure that is of known distance from the laser along the path of the laser beam and fixed with respect to the laser.

It is preferred that the interface may be a corneal shaped transparent element whereby the cornea is put into direct contact with the interface or contains an interface fluid between. Examples of patient interfaces devices are disclosed and taught in US Patent Application Publication Nos. 2010/0022994, 2011/0022035 and 2015/0088175, the entire disclosures of each of which are incorporated herein by reference.

Systems methods and apparatus for performing laser operations on the eye are disclosed and taught in US patent application Publication Nos. 2016/0302971, 2015/0105759, 2014/0378955, and U.S. Pat. Nos. 8,262,646 and 8,708,491, the entire disclosures of each of which are incorporated herein by reference.

Figure 7:
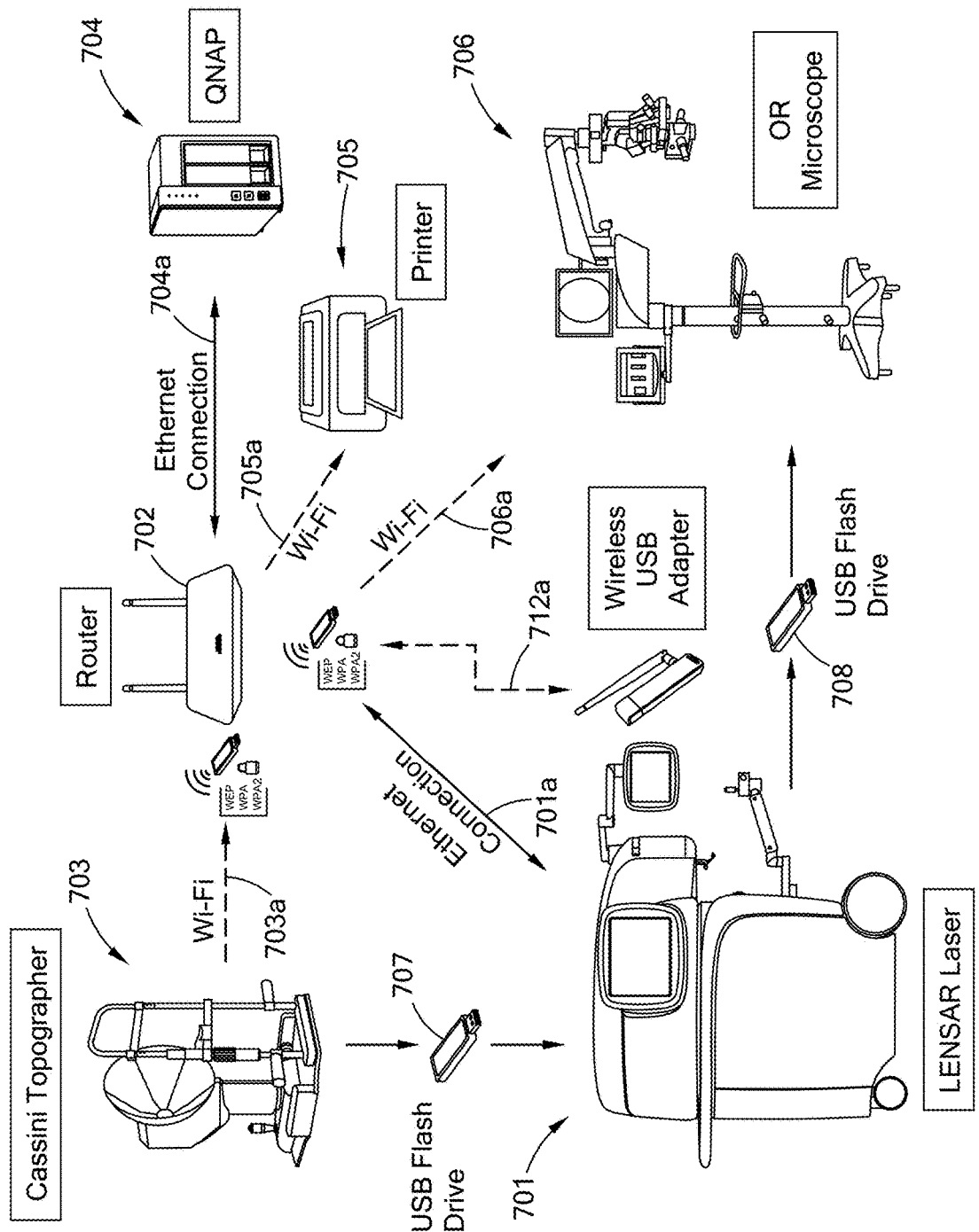
FIG. 7 shows a schematic of an embodiment of a networked laser system in accordance with the present inventions.
Figure 8:
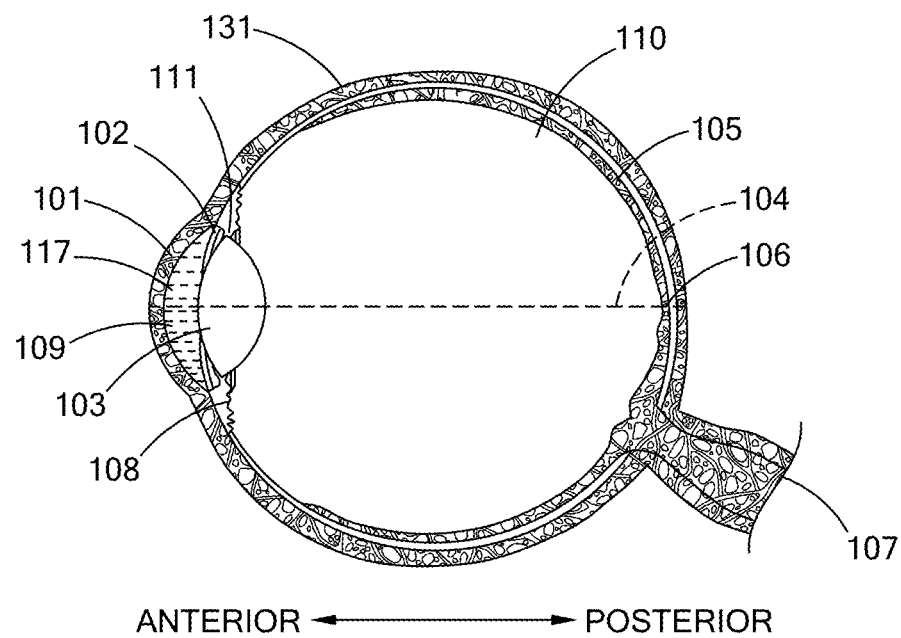
FIGS. 8 and 8A are cross sectional representations of the human eye.
Figure 8A:
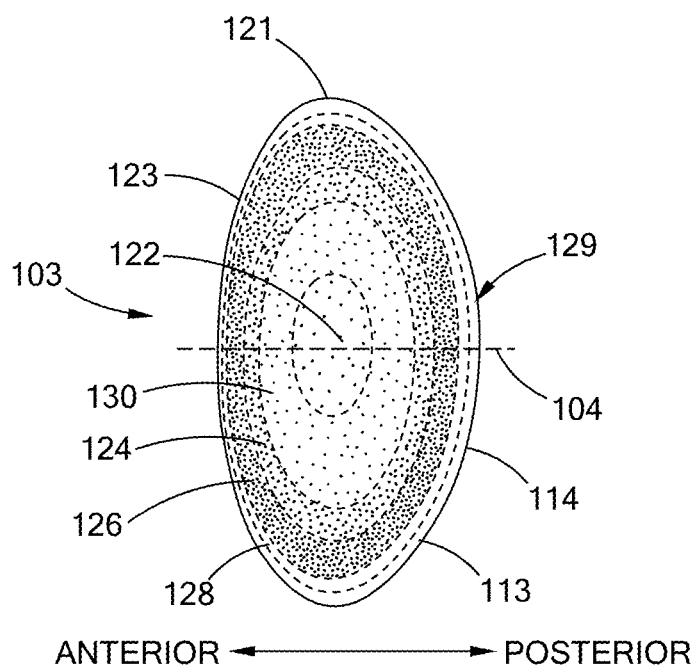

An embodiment of a network system for performing the laser procedures of the present inventions is provided in FIG. 7. This embodiment is a network, wherein the laser surgery system 701 is in communication with a Wi-Fi router 702. This may be by either an Ethernet connection 701a or Wi-Fi connection 702a or both. The router 702 is in turn in communication with a Cassini Topographer 703, A QNAP server 704, a printer 705, and an OR Microscope 706. The router is linked to these devices along communication pathways 703a, 704a, 705a, and 706a, respectively. This communication may be done either via a Wi-Fi connection, Ethernet link, other automation or data communication systems and combinations and variations of these. Data may be exchanged between the laser 701 and the Cassini Topographer 703 and the OR Microscope 706 via the use of USB Memory Sticks 707 or flash drive 708. This network may optionally include other devices useful in a hospital or a medical office, including personal computers or mobile devices. The network may download and/or upload a patient's medical history to a remote server. This information may include previously-acquired data regarding the patient's iris, and may be used by the system to ensure that the scanned iris belongs to the patient for whom the current treatment plan was developed. Other embodiments of combinations of the devices in this network are contemplated by the present inventions.

It is noted that there is no requirement to provide or address the theory underlying the novel and groundbreaking processes, laser operations, and laser patterns, enhanced and improved vision, or other beneficial features and properties that are the subject of, or associated with, embodiments of the present inventions. Nevertheless, various theories are provided in this specification to further advance the art in this area. The theories put forth in this specification, and unless expressly stated otherwise, in no way limit, restrict or narrow the scope of protection to be afforded the claimed inventions. These theories many not be required or practiced to utilize the present inventions. It is further understood that the present inventions may lead to new, and heretofore unknown theories to explain the function-features of embodiments of the methods, laser patterns, laser operations, functions of the eye, devices and system of the present inventions; and such later developed theories shall not limit the scope of protection afforded the present inventions.

The various embodiments of devices, systems, laser shot patterns, activities, and operations set forth in this specification may be used with, in or by, various measuring, diagnostic, surgical and therapeutic laser systems, in addition to those embodiments of the Figures and disclosed in this specification. The various embodiments of devices, systems, laser shot patterns, activities, and operations set forth in this specification may be used with: other measuring, diagnostic, surgical and therapeutic systems that may be developed in the future: with existing measuring, diagnostic, surgical and therapeutic laser systems, which may be modified, in-part, based on the teachings of this specification; and with other types of measuring, diagnostic, surgical and therapeutic systems. Further, the various embodiments of devices, systems, laser shot patterns, activities, and operations set forth in this specification may be used with each other in different and various combinations. Thus, for example, the configurations provided in the various embodiments of this specification may be used with each other; and the scope of protection afforded the present inventions should not be limited to a particular embodiment, configuration or arrangement that is set forth in a particular embodiment, example, or in an embodiment in a particular Figure.

The inventions may be embodied in other forms than those specifically disclosed herein without departing from their spirit or essential characteristics. The described embodiments are to be considered in all respects only as illustrative and not restrictive.

What is claimed:

1. A laser system for performing a laser operation to increase an amplitude of accommodation of a lens of an eye, the laser system comprising:
   a. a laser for generating a laser beam;
   b. a control system comprising a controller and a laser beam delivery pattern; and the control system configured to deliver the laser beam to the lens of the eye in the laser beam delivery pattern; and,
   c. the laser beam delivery pattern comprising an annular ring; and the control system configured to deliver the laser beam in the laser beam delivery pattern to a location below the lens capsule and entirely within the lens; wherein the laser beam delivery pattern avoids contact with an AP pillar of lens material and an equatorial pillar of lens material;
      i. whereby after delivery of the laser beam pattern an AP pillar and an equatorial pillar of laser unaffected lens material remains;
      ii. whereby after delivery of the laser beam pattern an annular shape changing zone is created within the lens and extends to and includes the lens capsule;
   d. wherein the laser beam delivery pattern comprises a plurality of shots, wherein all laser beams in the laser beam shot pattern are below laser induced optical breakdown at the lens capsule.

2. The system of claim 1, wherein the laser beam delivery pattern comprises a second annular ring.

3. The system of claim 2, wherein the laser beam delivery pattern comprises a second annular ring; wherein the annular rings follow a shape of the lens capsule, and wherein the annular rings do not contact an equatorial axis of the lens.

4. The system of claim 3, wherein the laser beam delivery pattern comprises a plurality of shots having a predetermined power density at the lens capsule and within the lens; and wherein the AP pillar has a cross sectional diameter of about 1 mm to about 2 mm.

5. The systems of claim 1, 2, 3 or 4, wherein the laser beam delivery pattern comprises a plurality of shots, wherein the laser shots have a pulse length, and a spot size at the focal point; and
   wherein the AP pillar defines an axis; and the AP pillar axis is coaxial with an AP axis of the eye.

6. The systems of claim 1, 2, 3, or 4, wherein the laser beam delivery pattern comprises a plurality of shots, wherein the laser shots have a pulse length, and a spot size at the focal point; and
   wherein the AP pillar defines an axis; and the AP pillar axis is not coaxial with an AP axis of the eye.

7. The systems of claim 1, 2, 3, or 4, wherein the AP pillar defines an axis; and the AP pillar axis is not coaxial and is titled with an AP axis of the eye.

8. The systems of claim 1, 2, 3, or 4, wherein the laser beam delivery pattern comprises a second annular ring; and
   wherein the AP pillar defines an axis; and the AP pillar axis is not coaxial with an AP axis of the eye.

9. The systems of claim 1, 2, 3, or 4, wherein the laser beam delivery pattern comprises a second annular ring; wherein the annular rings follow a shape of the lens capsule, and wherein the annular rings do not contact an equatorial axis of the lens; and wherein the AP pillar defines an axis; and the AP pillar axis is not coaxial and is titled with an AP axis of the eye.

10. A laser system for performing a laser operation to increase an amplitude of accommodation of a lens of an eye, the laser system comprising:
    a. a laser for generating a laser beam;
    b. a control system comprising a controller and a laser beam delivery pattern; and the control system configured to deliver the laser beam to the lens of the eye in the laser beam delivery pattern; and,
    c. the laser beam delivery pattern comprising an annular ring; and the control system configured to deliver the laser beam in the laser beam delivery pattern to a location below the lens capsule and entirely within the lens; wherein the laser beam delivery pattern avoids contact with an AP pillar of lens material and an equatorial pillar of lens material;
       i. whereby after delivery of the laser beam delivery pattern an AP pillar and an equatorial pillar of laser unaffected lens material remains;
       ii. whereby after delivery of the laser beam delivery pattern an annular shape changing zone is created within the lens and extends to and includes the lens capsule;
       iii. whereby the annular ring defines a volume of lens material of about 4.0 mm$^3$ to about 75 mm$^3$; and a surface area to volume ratio of about 2 to about 5.

11. The system of claim 10, wherein the volume is from about 20 mm$^3$ to about 40 mm$^3$.

12. The system of claim 10, wherein the surface area to volume ratio is about 3 to about 4.

13. The system of claim 10, wherein the laser beam delivery pattern comprises a plurality of shots, wherein all laser beams in the laser beam shot pattern are below laser induced optical breakdown at the lens capsule.

* * * * *